US00PP30589P2

(12) United States Plant Patent
Sproul

(10) Patent No.: US PP30,589 P2
(45) Date of Patent: Jun. 25, 2019

(54) FLORIBUNDA ROSE PLANT NAMED 'SPROLEMANGO'

(50) Latin Name: *Rosa hybrida*
Varietal Denomination: SPROLEMANGO

(71) Applicant: THE CONARD-PYLE COMPANY, West Grove, PA (US)

(72) Inventor: James Sproul, Bakersfield, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/932,720

(22) Filed: Apr. 13, 2018

(51) Int. Cl.
*A01H 5/02* (2018.01)
*A01H 6/74* (2018.01)

(52) U.S. Cl.
USPC ..... Plt./143
CPC ..... *A01H 6/74* (2018.05); *A01H 5/02* (2013.01)

(58) Field of Classification Search
USPC ..... Plt./147, 146, 145, 143
CPC ..... A01H 5/0222
See application file for complete search history.

(56) References Cited

U.S. PATENT DOCUMENTS

PP25,125 P3 12/2014 Sproul

*Primary Examiner* — Kent L Bell
(74) *Attorney, Agent, or Firm* — Buchanan Ingersoll & Rooney PC

(57) ABSTRACT

A new and distinct variety of Floribunda Rose plant, herein referred to by its cultivar name, 'SPROLEMANGO', is provided which forms in abundance on a substantially continuous basis attractive, cup-like apricot colored blossoms with a red center. The vegetation is vigorous and the growth habit is very bushy and compact. Attractive, glossy, dark green foliage is formed. The disease resistance is good. The new variety is well suited for proving attractive ornamentation in the landscape.

1 Drawing Sheet

Botanical/commercial classification:
Latin name—*Rosa hybrida.*
Common name—Floribunda Rose Plant.
Varietal denomination: 'SPROLEMANGO'.

SUMMARY OF THE INVENTION

The new variety of *Rosa hybrida* Floribunda rose plant was created by artificial pollination in April, 2011 at Bakersfield, Calif., U.S.A., wherein two parents were crossed which previously had been studied in the hope that they would contribute the desired characteristics. The female parent (i.e., the seed parent) was an unnamed and unreleased seedling. The male parent (i.e, the pollen parent) was an unnamed and unreleased seedling.

The parentage of the new variety can be summarized as follows:

unnamed seedling x unnamed seedling

The seeds resulting from the above pollination were sown and small plants were obtained which were physically and biologically different from each other. Selective study resulted in the identification of a single plant of the new variety.

It was found that the new variety of Floribunda rose plant of the present invention:

(a) abundantly and substantially continuously forms attractive, semi-double, cuplike shaped, apricot colored blossoms with red center,
(b) forms a very bushy and compact growth habit,
(c) has vigorous vegetation,
(d) forms attractive ornamental glossy, dark green foliage, (e) exhibits good tolerance to diseases, and
(f) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the female parent (i.e., the seed parent) displays yellow colored blooms without a red center, whereas the new variety displays apricot colored blooms with a red center. Additionally, the new variety can be readily distinguished from other Floribunda roses, such as the 'Spromel' variety (U.S. Plant Pat. No. 25,125) in that the new variety displays a compact growth habit and is smaller than the 'Spromel' variety, which displays an upright growth habit.

The new variety has been found to undergo asexual propagation in Wasco, Calif., U.S.A by a number of routes, including budding, grafting, and the use of cuttings. Asexual propagation by the above-mentioned techniques in Wasco, Calif., U.S.A. has shown that the characteristics of the new variety are stable and are strictly transmissible by such asexual propagation from one generation to another. Accordingly, the new variety undergoes asexual propagation in a true-to-type manner.

The new variety has been named 'SPROLEMANGO'.

BRIEF DESCRIPTION OF THE PHOTOGRAPH

The accompanying photograph shows as nearly true as it is reasonably possible to make the same, in a color illustration of this character, a typical specimen of the plant parts of the new variety. The rose plant of the new variety was approximately two years of age and was observed during July 2017 while budded on its own roots and growing outdoors at West Grove, Pa., U.S.A.

FIG. 1—illustrates specimens of typical blossoms.

DETAILED BOTANICAL DESCRIPTION

The chart used in the identification of the colors is that of The Royal Horticultural Society (R.H.S. Colour Chart), 2015, London, England. The terminology which precedes reference to the chart has been added to indicate the corresponding color in more common terms. The description is based on the observation of two-year-old specimens of the new variety during July while growing in a container on its own roots and growing outdoors at West Grove, Pa., U.S.A.

Class: Floribunda Rose Plant.

Plant:

*Habit*.—Very compact and busy.

*Height*.—Approximately up to 3 feet at maturity on average.

*Width*.—Approximately up to 2.5 feet at maturity on average.

Branches:

*Color*.—Young stems: commonly near Yellow-Green Group 144B. Adult wood: commonly near Yellow-Green Group 144A.

*Length*.—Main stems: approximately 60.0 cm on average. Secondary stems: approximately 13.0 cm on average.

*Diameter*.—Approximately 4.0 mm on average.

*Thorns*.—Young thorns: color is commonly near Greyed-Orange Group 176C, length is approximately 4.0 mm on average and width is approximately 4.0 mm on average at point of attachment. Old thorns: color is commonly near Grey-Brown Group N199C, length is approximately 1.0 cm on average, and width is approximately 4.0 mm on average at the point of attachment.

Foliage:

*General appearance*.—Glossy.

*New foliage*.—Upper surface color: commonly near Green Group 137A. Under surface color: commonly near Yellow-Green Group 146B.

*Adult foliage*.—Upper surface color: commonly near Green Group 139A. Under surface color: commonly near Green Group 137C.

Leaves:

*Leaf margin*.—Serrate.

*5-leaflet leaf*.—Length: approximately 9.0 cm on average. Width: approximately 5.0 cm on average.

*Petioles*.—Length: approximately 2.4 cm on average. Diameter: approximately 2.0 mm on average. Color: commonly near Yellow-Green Group 146B.

*Petiole rachis*.—Length: approximately 6.0 cm on average. Diameter: approximately 2.0 mm on average. Color: commonly near Yellow-Green Group 146B.

*Leaflets*.—Number of leaflets: 3, 5, and 7. Shape: ovate, apex is rounded to acute, and base is rounded. Texture: smooth. Terminal leaflet: length is approximately 5.0 cm on average and width is approximately 4.0 cm on average; petiole diameter is approximately 1.0 mm on average. Lower leaflets: length is approximately 3.5 cm on average and width is approximately 3.5 cm on average.

Inflorescence:

*Number of flowers per stem*.—Generally between 1 and 4 flowers per stem on average.

*Number of flowers per plant*.—Generally about 15 blooms on average per plant at once.

*Lastingness of the bloom*.—Approximately 5 days.

*Bud*.—Shape: ovoid. Length: approximately 2.5 cm on average. Width: approximately 1.5 cm on average. Color when opening: commonly near Yellow-Orange Group 19A and Yellow Group 7B.

*Sepals*.—Number: commonly 5. Length: approximately 1.7 cm on average. Width: approximately 7.0 mm on average. Margin: entire with extension on three sepals measuring 8.0 mm in length and 2.0 mm in width. Upper surface color and texture: commonly covered in short pubescence and commonly near Green Group 143C. Under surface color and texture: commonly puberulent and commonly near Green Group 143B.

*Receptacle*.—General: achenes stand on the bottom and wall. Color: commonly near Green Group 143B. Width: approximately 1.0 cm on average. Depth: approximately 1.0 cm on average. Surface: smooth. Shape: round.

*Peduncle*.—Length: approximately 3.5 cm on average. Diameter: approximately 3.0 mm on average. Surface: moderately covered in short, flexible thorns that measure less than 2.0 mm in length. Color: commonly near Green Group 143B.

*Flower*.—Average diameter when fully open: approximately near 6 to 8 cm on average. Depth: approximately 3.5 cm on average. Form: semi-double, cup-like. Number of petals under normal conditions: approximately 9 to 12 petals on average. Shape of the petal: overall broadly obovate. Base: rounded. Apex: obtuse with a slightly wavy margin. Margin: entire. Petal length: approximately 2.5 cm on average. Petal width: approximately 2.0 cm on average. Petal drop: good. Fragrance: slight. Color when opening: Upper surface: commonly near Yellow-Orange Group 22C towards the apex, transitioning to near Yellow Group 12A towards the middle and near Red Group 42A towards the base; and point of attachment is commonly near Yellow-Orange Group 17A. Under surface: commonly near Yellow Group 13C and point of attachments is commonly near Yellow Group 13B. Color at the end of blooming: Upper surface: commonly near Red-Purple Group 62C towards the apex, transitioning to near Yellow Group 11C towards the middle and near Red Group 45D towards the base; and point of attachment is commonly near Yellow Group 13B. Under surface: commonly near Red Group 36C and point of attachment is commonly near Yellow-White Group 158C. Stamen: number is approximately 100 on average. Anthers: number is approximately 100 on average and coloration is commonly near Yellow-Orange Group 22B. Filaments: length is approximately 7.0 mm on average and coloration is commonly near Yellow-Orange Group 21C. Pistils: arrangement is separate and free and number is approximately 35 on average. Styles: length is approximately 3.0 mm on average and the coloration is commonly near Yellow-Green Group 149C. Stigmas: size is approximately 1.0 mm on average and the coloration is commonly near Yellow-Green Group 150D. Pollen: coloration is commonly near Yellow Group 4B. Hips: not available at this stage.

Development:

*Vegetation*.—Dark green, glossy, vigorous, and strong.

*Blooming*.—Abundant and substantially continuous from spring through frost, typically from June to November in Southeastern Pennsylvania.

*Tolerance to disease*.—Good, and particularly against black spot, rust, and *Sphaerotheca pannosa* mildews.

The new 'SPROLEMANGO' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda rose plant characterized by the following combination of characteristics:

(a) abundantly and substantially continuously forms attractive, semi-double, cuplike shaped, apricot colored blossoms with red center, (b) forms a very bushy and compact growth habit, (c) has vigorous vegetation, (d) forms attractive ornamental glossy, dark green foliage, (e) exhibits good tolerance to diseases, and (f) is well suited for providing attractive ornamentation; substantially as herein shown and described.

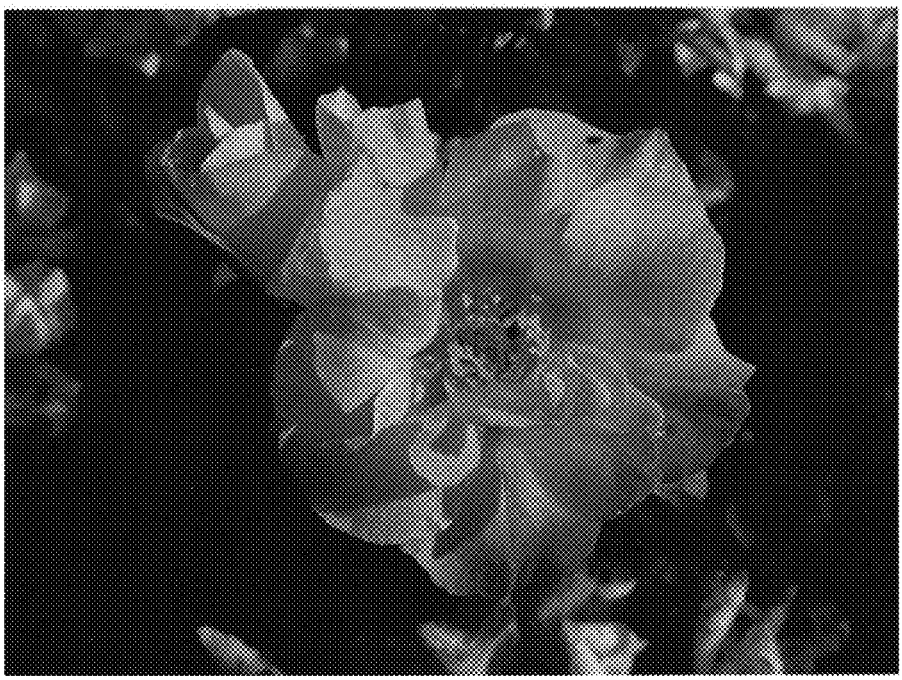

* * * * *